(12) United States Patent
Tani et al.

(10) Patent No.: US 10,166,040 B2
(45) Date of Patent: Jan. 1, 2019

(54) ORGAN RESECTION TOOL

(71) Applicant: National University Corporation Shiga University of Medical Science, Shiga (JP)

(72) Inventors: Tohru Tani, Shiga (JP); Shigeyuki Naka, Shiga (JP); Hiroya Akabori, Shiga (JP)

(73) Assignee: National University Corporation Shiga University Of Medical Science, Shiga (JP)

( * ) Notice: Subject to any disclaimer, the term of this patent is extended or adjusted under 35 U.S.C. 154(b) by 190 days.

(21) Appl. No.: 14/400,857

(22) PCT Filed: May 14, 2013

(86) PCT No.: PCT/JP2013/063471
§ 371 (c)(1),
(2) Date: Nov. 13, 2014

(87) PCT Pub. No.: WO2013/172361
PCT Pub. Date: Nov. 21, 2013

(65) Prior Publication Data
US 2015/0141977 A1 May 21, 2015

(30) Foreign Application Priority Data
May 14, 2012 (JP) .................... 2012-110317

(51) Int. Cl.
*A61B 18/18* (2006.01)
*A61B 17/32* (2006.01)
*A61B 18/00* (2006.01)

(52) U.S. Cl.
CPC .. *A61B 17/320068* (2013.01); *A61B 18/1815* (2013.01); *A61B 17/32* (2013.01);
(Continued)

(58) Field of Classification Search
CPC ............ A61B 18/15; A61B 2018/1823; A61B 2018/183; A61B 2018/1838;
(Continued)

(56) References Cited

U.S. PATENT DOCUMENTS 5,944,715 A     8/1999   Goble et al.
5,948,009 A *   9/1999   Tu ...................... A61B 18/1485
                                                                                                                  606/169
(Continued)

FOREIGN PATENT DOCUMENTS

DE       3707921 A1    9/1987
GB       2320683 A     7/1998
(Continued)

OTHER PUBLICATIONS

International Search Report and Written Opinion issued in corresponding International Patent Application No. PCT/JP2013/063471 dated Aug. 20, 2013 (5 pages).

(Continued)

*Primary Examiner* — Jaymi Della
(74) *Attorney, Agent, or Firm* — Kilyk & Bowersox, P.L.L.C.

(57) ABSTRACT

It is an object to provide a surgical tool for excising a hard solid organ such as cirrhotic liver or cutting the organ into a groove without causing bleeding. The inventors of the present invention have found that an organ resection tool including a brush-like structure capable of performing microwave irradiation and/or a brush-like structure capable of receiving a microwave can achieve the above-mentioned object, to thereby arrive at the present invention (organ resection tool including a brush structure capable of performing microwave irradiation). For example, an organ can be crushed or scraped away by manually abrading the organ with a brush of a solid organ resection tool including a brush (Continued)

structure capable of performing microwave irradiation according to the present invention. Further, the organ can be concurrently coagulated through the microwave irradiation to stop bleeding.

18 Claims, 12 Drawing Sheets

(52) U.S. Cl.
CPC ............ *A61B 2017/320012* (2013.01); *A61B 2017/320072* (2013.01); *A61B 2018/0019* (2013.01); *A61B 2018/00267* (2013.01); *A61B 2018/00529* (2013.01); *A61B 2018/00589* (2013.01); *A61B 2018/00601* (2013.01); *A61B 2018/1861* (2013.01); *A61B 2018/1892* (2013.01); *A61B 2218/002* (2013.01); *A61B 2218/007* (2013.01)

(58) Field of Classification Search
CPC .... A61B 2018/1846; A61B 2018/1853; A61B 2018/1861; A61B 2018/1869; A61B 2018/1876; A61B 2018/1884; A61B 2018/1892
See application file for complete search history.

(56) References Cited

U.S. PATENT DOCUMENTS

| | | | | |
|---|---|---|---|---|
| 6,233,490 | B1* | 5/2001 | Kasevich | A61B 18/18 606/33 |
| 6,652,516 | B1* | 11/2003 | Gough | A61B 18/1477 606/41 |
| 2004/0260282 | A1* | 12/2004 | Gough | A61B 18/1477 606/41 |
| 2005/0159740 | A1 | 7/2005 | Paul et al. | |
| 2008/0266203 | A1* | 10/2008 | Rossetto | A61B 18/18 343/895 |
| 2009/0198227 | A1 | 8/2009 | Prakash | |
| 2010/0030207 | A1* | 2/2010 | Hancock | A61B 18/1815 606/33 |

FOREIGN PATENT DOCUMENTS

| | | |
|---|---|---|
| JP | S62-1605 U | 1/1987 |
| JP | H05-84255 A | 4/1993 |
| JP | 09-028716 A | 2/1997 |
| JP | 2001-061847 | 3/2001 |
| JP | 2003-111770 A | 4/2003 |
| WO | 9517855 A1 | 7/1995 |
| WO | 2005096967 A2 | 10/2005 |
| WO | 2008044000 A1 | 4/2008 |
| WO | 2008044013 A2 | 4/2008 |
| WO | 2008147773 A1 | 12/2008 |

OTHER PUBLICATIONS

Extended European Search Report issued in corresponding European Patent Application No. 13790477.7 dated Feb. 10, 2016 (8 pages).

Office Action received in corresponding Japanese Patent Application No. 2014-515647 dated Nov. 18, 2016 (5 pages) (English translation only).

* cited by examiner

DOUBLE TUBE

ORGAN RESECTION TOOL

The present application is a National Stage Application of PCT/JP2013/063471, filed May 14, 2013, which claims priority from Japanese Patent Application No. 2012-110317, filed May 14, 2012.

TECHNICAL FIELD

The present invention relates to an organ resection tool having a microwave irradiation function, and more particularly, to a solid organ resection tool.

More specifically, the present invention relates to an organ resection tool including a brush-like structure capable of performing microwave irradiation and/or a brush-like structure capable of receiving a microwave, and to an organ resection tool including vibration function means with a tip end portion positioned in a microwave irradiation range.

Note that, the present application claims priority from Japanese Patent Application No. 2012-110317, the disclosure of which is incorporated herein by reference.

BACKGROUND ART

Solid organs (brain, liver, spleen, kidney, pancreas, etc.) have a large number of small blood vessels, resulting in such a structure that the solid organs may bleed wherever the solid organs are cut. In particular, as soft solid organs having a considerable number of capillary blood vessels, liver, pancreas, spleen, and kidney are given. Besides, the solid organs are not strong tissues unlike luminal organs although the solid organs are harder than soybean curd. When a transducer is brought into contact with the solid organ, the solid organ is sonicated, and hence the cell tissue thereof falls apart so that the solid organ is cut while being punctured.

In the case of thinly excising organ tissues for excision of the above-mentioned organs, an ultrasonic coagulation cutter and a radio-frequency coagulation cutter have mainly been used. However, in the case of excising an organ site having a depth of 1 cm or more, blood vessels thereof are thick, and hence the ultrasonic coagulation cutter and the radio-frequency coagulation cutter cannot be used. Thus, in the case of excising a deeper organ site, an ultrasonic aspirator (CUSA, etc.) using a high-frequency wave or ultrasonic vibration (cavitation) has been used. However, even with those tools, slight bleeding cannot be suppressed sufficiently. Further, in the cirrhotic liver tissue in which the liver tissue is hard, in spite of the fact that liver cancer is, in particular, liable to occur, the resection performance of the ultrasonic aspirator is insufficient. Accordingly, in actuality, surgical tools cannot sufficiently excise the cirrhotic liver that is most liable to bleed and is found in many cases.

Further, commercially available medical instruments are configured to destroy organ tissue with a transducer, inject water into the destroyed organ tissue so as to wash the organ tissue away, and aspirate the organ tissue. This operation is repeated to resect a solid organ in a fine blood vessel portion. The transducer includes an ultrasonic transducer for generating an ultrasonic wave and a transmission member for transmitting, to a target, the ultrasonic wave generated by the ultrasonic transducer (Patent Literature 1).

In a surgical tool having a microwave irradiation function, a needle-like probe for performing microwave irradiation outputs a microwave only from a tip end thereof. On the other hand, the inventors of the present invention have confirmed that a surgical tool having a microwave irradiation function with halved coaxial cable-like structures is capable of outputting a microwave even in a long line extending from the center to the outside along the halved structures (Patent Literature 2).

However, in actuality, there is no surgical tool capable of concurrently performing both the destruction of an organ, in particular, a solid organ and the hemostasis by the coagulation of tissue.

A surgical tool using a transducer and a high-frequency current in combination has been reported. This surgical tool is a surgical instrument "comprising: a hand piece equipped with a treatment section arranged at the tip side thereof to treat living body tissue and including a probe to be supplied with a high frequency current according to a directive and an ultrasonic transducer rigidly secured to the probe and adapted to ultrasonically oscillate the probe; a high frequency drive circuit which supply a high frequency current to the probe; and an ultrasonic transducer drive circuit which drive the ultrasonic transducer, the ultrasonic transducer drive circuit being adapted to control the amplitude of ultrasonic oscillations at the treatment section according to the magnitude of the impedance value as detected by the high frequency drive circuit at the time of outputting a high frequency current" (Patent Literature 3). However, this instrument is provided only for the purpose of preventing the burning of living tissue, which may be caused by a scalpel top electrode.

CITATION LIST

Patent Literature

[PTL 1] JP 2011-206094 A
[PTL 2] JP 2008-54926 A
[PTL 3] JP 2008-055151 A

SUMMARY OF INVENTION

Technical Problem

The present invention mainly has two objects.
(Object 1)

As cutting tools for organs, in particular, solid organs, ultrasonic aspirators have been mainly used. However, these cutting tools cannot exhibit sufficient effects with respect to hard organs, and the hemostasis effect thereof is also insufficient. Further, these cutting tools require high-speed vibration causing cavitation, and hence the device of each tool is enlarged. A conductive wire connected to a portion of the tool, which is held by a hand of an operator, is thick and heavy, thereby imposing restrictions on operations. Further, the cutting tools are expensive.

Accordingly, it is an object of the present invention to provide a surgical tool capable of excising a hard solid organ such as cirrhotic liver or cutting the organ into a groove without causing bleeding.

(Object 2)

The related-art solid organ cutting tool can be used for crushing, washing away, aspirating, and cutting off a solid organ. However, thin blood vessels are also crushed to cause bleeding, and hence the hemostasis function of the related-art solid organ cutting tool is weak. Thus, bleeding occurs continuously in a surgical operation field although it is not heavy bleeding, thereby being difficult for an operator to observe the surgical operation field and to perform a surgical operation. To address this, a hemostasis operation is separately required.

Accordingly, it is another object of the present invention to provide a surgical tool capable of concurrently performing hemostasis while crushing a solid organ.

Solution to Problem

The inventors of the present invention have studied diligently so as to achieve Object 1, and as a result, found that Object 1 can be achieved by an organ resection tool including a brush-like structure capable of performing microwave irradiation and/or a brush-like structure capable of receiving a microwave, to thereby arrive at the present invention (organ resection tool including a brush structure capable of performing microwave irradiation).

For example, an organ can be crushed or scraped away by manually abrading the organ with a brush of a solid organ resection tool including a brush structure capable of performing microwave irradiation according to the present invention. Further, the organ can be concurrently coagulated through the microwave irradiation to perform hemostasis.

Further, the inventors of the present invention have studied diligently so as to achieve Object 2, and as a result, found that Object 2 can be achieved by an organ resection tool having a feature in that a tip end portion of vibration function means (transducer) is positioned in a microwave irradiation range, to thereby arrive at the present invention (organ resection tool including vibration function means with a tip end portion positioned in a microwave irradiation range).

The organ resection tool including vibration function means with a tip end portion positioned in a microwave irradiation range according to the present invention is capable of crushing tissue in the microwave irradiation range while coagulating the tissue to perform hemostasis.

That is, the present invention includes the following embodiments.

1. An organ resection tool, including a brush-like structure capable of performing microwave irradiation and/or a brush-like structure capable of receiving a microwave.

2. An organ resection tool according to Embodiment 1, in which the organ resection tool includes the brush-like structure capable of performing microwave irradiation and the brush-like structure capable of receiving a microwave.

3. An organ resection tool according to Embodiment 1 or 2, in which the brush-like structure capable of performing microwave irradiation is connected to a central conductor directly or indirectly, and in which the brush-like structure capable of receiving a microwave is connected to an external conductor directly or indirectly.

4. An organ resection tool according to any one of Embodiments 1 to 3, in which the central conductor avoids contact with the external conductor through intermediation of an insulator or via an air gap.

5. An organ resection tool according to any one of Embodiments 1 to 4, including the following configuration:

(1) the central conductor having a cylindrical shape;

(2) the insulator covering a part or all of the central conductor;

(3) the external conductor covering a part or all of the insulator;

(4) the brush-like structure capable of performing microwave irradiation being connected to the central conductor directly or indirectly; and (5) the brush-like structure capable of receiving a microwave being connected to the external conductor directly or indirectly.

6. An organ resection tool according to any one of Embodiments 1 to 4, including the following configuration:

(1) the central conductor having a cylindrical shape with a hollow formed therein;

(2) a hollow tube (hollow structure) formed by the hollow;

(3) the insulator covering a part or all of the central conductor;

(4) the external conductor covering a part or all of the insulator;

(5) the brush-like structure capable of performing microwave irradiation being connected to the central conductor directly or indirectly; and (6) the brush-like structure capable of receiving a microwave being connected to the external conductor directly or indirectly.

7. An organ resection tool according to any one of Embodiments 1 to 4, including the following configuration:

(1) the central conductor having a cylindrical shape with a hollow formed therein;

(2) a hollow tube (hollow structure) formed by the hollow;

(3) the insulator covering a part or all of the central conductor;

(4) the external conductor covering a part or all of the insulator; and (5) the brush-like structure capable of performing microwave irradiation being formed by the central conductor, the insulator, and the external conductor.

8. An organ resection tool according to Embodiment 6 or 7, in which the hollow tube includes an aspiration tube and/or a water feed tube.

9. An organ resection tool according to any one of Embodiments 1 to 8, in which the brush-like structure is made of iron, copper, titanium, stainless steel, phosphor bronze, or brass.

10. An organ resection tool according to any one of Embodiments 1 to 9, in which a length of one piece of the brush-like structure falls within a range of from 0.5 mm to 25 mm, a range of from 1.0 mm to 20 mm, or a range of from 5.0 mm to 15 mm.

11. An organ resection tool according to any one of Embodiments 1 to 10, in which a diameter of one piece of the brush-like structure falls within a range of from 0.1 mm to 0.5 mm, a range of from 0.2 mm to 0.5 mm, or a range of from 0.3 mm to 0.5 mm.

12. An organ resection tool according to any one of Embodiments 1 to 11, in which an entire horizontal width of the brush-like structure falls within a range of from 0.2 mm to 3 cm, a range of from 0.5 mm to 2.0 cm, a range of from 0.6 mm to 1.5 cm, or a range of from 0.7 mm to 11 mm.

13. An organ resection tool according to any one of Embodiments 1 to 12, in which the brush-like structure includes one or a plurality of rows of a transverse brush, a random arrangement brush, one or a plurality of rows of a circular arrangement brush, or one or a plurality of rows of a semi-circular arrangement brush.

14. An organ resection tool according to any one of Embodiments 1 to 13, in which the brush-like structure has a loop shape, and is curved in an inward direction at a tip end of the brush-like structure.

15. An organ resection tool according to any one of Embodiments 1 to 14, in which the brush-like structure includes an elastic member, and in which the brush-like structure is capable of applying a pressure to living tissue when being brought into contact with the living tissue.

16. An organ resection tool according to any one of Embodiments 1 to 15, further including vibration function means capable of vibrating the brush-like structure.

17. An organ resection tool, including:
a central conductor;
an external conductor; and
vibration function means,
in which a tip end portion of the vibration function means is positioned in a microwave irradiation range.

18. An organ resection tool according to Embodiment 17, in which the central conductor and the external conductor form a ring shape through intermediation of an insulator, and in which the tip end portion of the vibration function means is positioned in a microwave irradiation range defined by the ring shape.

19. An organ resection tool according to Embodiment 17, in which the central conductor and the external conductor have bar-like structures or needle-like structures, respectively, which are formed independently from each other, and in which the tip end portion of the vibration function means is positioned in a microwave irradiation range defined by the central conductor and the external conductor.

20. An organ resection tool according to Embodiment 17, including the following configuration:

(1) the central conductor having a cylindrical shape;
(2) an insulator covering a part or all of the central conductor;
(3) the external conductor covering a part or all of the insulator;
(4) the vibration function means;
(5) the central conductor being exposed in a longitudinal axis direction without being partly covered with the insulator and the external conductor; and
(6) the tip end portion of the vibration function means being positioned in a microwave irradiation range defined by the exposed central conductor and the external conductor.

21. An organ resection tool according to Embodiment 17, including the following configuration:

(1) the central conductor having a cylindrical shape with a hollow formed therein;
(2) a hollow tube (hollow structure) formed by the hollow;
(3) an insulator covering a part or all of the central conductor;
(4) the external conductor covering a part or all of the insulator;
(5) the vibration function means;
(6) a brush-like structure capable of performing microwave irradiation being formed by the central conductor, the insulator, and the external conductor; and
(7) the tip end portion of the vibration function means being positioned in a microwave irradiation range defined by the exposed central conductor and the external conductor.

Advantageous Effects of Invention (Organ Resection Tool Including Brush Structure Capable of Performing Microwave Irradiation)

The organ resection tool including a brush structure capable of performing microwave irradiation according to the present invention provides an inexpensive solid organ resection tool with a simple structure capable of crushing, cutting, scraping off, washing away as desired, and/or aspirating an organ (in particular, a solid organ) with the brush structure, and concurrently stopping, through microwave irradiation, bleeding from fine blood vessels on the periphery of the organ that has been scraped off.

Note that, the inventors of the present invention have provided a surgical tool including a brush structure serving as a capillary aspiration cannula. Although the surgical tool includes an aspiration tube including a coagulation device, the purpose of the aspiration tube is to aspirate an organ without damaging the organ. That is, the organ resection tool including a brush structure capable of performing microwave irradiation according to the present invention is completely different from the surgical tool including a brush structure serving as a capillary aspiration cannula.

(Organ Resection Tool Including Vibration Function Means with Tip End Portion Positioned in Microwave Irradiation Range)

The organ resection tool including vibration function means with a tip end portion positioned in a microwave irradiation range according to the present invention provides an inexpensive organ resection tool with a simple structure capable of crushing, washing away, and further as desired, aspirating an organ (in particular, a solid organ) with the vibration function means, and concurrently stopping, through microwave irradiation, bleeding from fine blood vessels on the periphery of the crushed organ. Accordingly, a cutting line of an organ becomes easy to observe, and blood vessels and the like of an organ, which need to be left, can be visually recognized easily.

BRIEF DESCRIPTION OF DRAWINGS

FIG. 1 illustrates, on the right side, a situation where a microwave is radiated from the brush structure.

DESCRIPTION OF EMBODIMENTS

Figure 1:
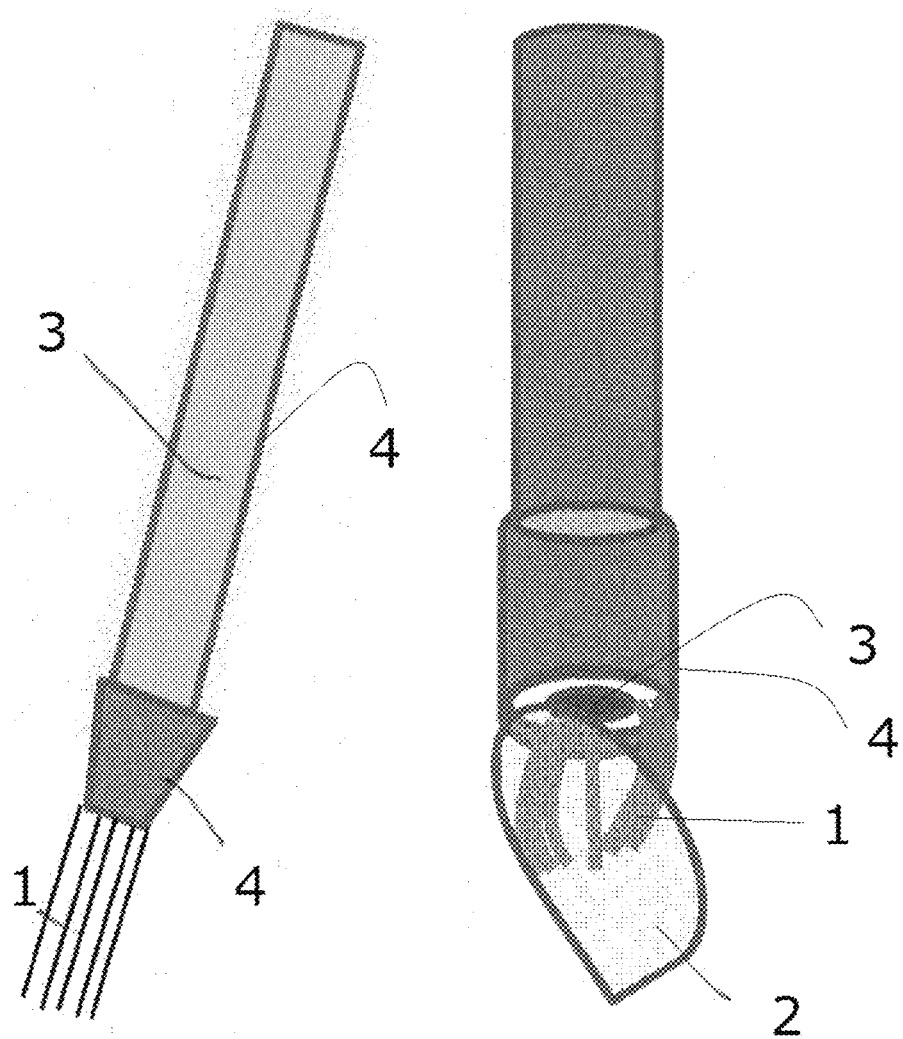
FIG. 1 is an entire view of an organ resection tool including a brush structure capable of performing microwave irradiation.

The "organ resection tool including a brush structure capable of performing microwave irradiation" and the "organ resection tool including vibration function means with a tip end portion positioned in a microwave irradiation range" according to the present invention are hereinafter described with reference to the drawings. Note that, the present invention is not limited to the organ resection tool illustrated in the drawings.

(Features of Organ Resection Tool Including Brush Structure Capable of Performing Microwave Irradiation)

The organ resection tool including a brush structure capable of performing microwave irradiation according to the present invention has a feature in that the organ resection tool includes a brush-like structure capable of performing microwave irradiation and/or a brush-like structure capable of receiving a microwave. Specifically, the brush structure capable of performing microwave irradiation has a microwave irradiation probe function.

Further, the organ resection tool preferably has a feature in that the brush-like structure capable of performing microwave irradiation is connected to a central conductor directly or indirectly, and/or the brush-like structure capable of receiving a microwave is connected to an external conductor directly or indirectly. Note that, as needed, the central conductor is configured so as not to be held in contact with the external conductor through intermediation of an insulator or via an air gap.

Due to the above-mentioned features, the organ resection tool has the following configuration.

(1) A microwave is output from the brush structure capable of performing microwave irradiation to the brush-like structure capable of receiving a microwave, and hemostasis can be performed with the microwave while an organ is destroyed with the brush structure.

(2) A microwave is output from the brush structure capable of performing microwave irradiation to the external conductor, and hemostasis can be performed with the microwave while an organ is destroyed with the brush structure.

(3) A microwave is output from the central conductor to the brush-like structure capable of receiving a microwave, and hemostasis can be performed with the microwave while an organ is destroyed with the brush structure.

(Configuration of Organ Resection Tool Including Brush Structure Capable of Performing Microwave Irradiation)

The organ resection tool including a brush structure capable of performing microwave irradiation according to the present invention preferably has the following configuration but is not limited thereto.

The organ resection tool includes the following configuration:

(1) the central conductor having a cylindrical shape;

(2) the insulator covering a part or all of the central conductor;

(3) the external conductor covering a part or all of the insulator;

(4) the brush-like structure capable of performing microwave irradiation being connected to the central conductor directly or indirectly; and (5) the brush-like structure capable of receiving a microwave being connected to the external conductor directly or indirectly.

The organ resection tool includes the following configuration (see FIGS. 5 and 6):

(1) the central conductor having a cylindrical shape with a hollow formed therein;

(2) a hollow tube (hollow structure) formed by the hollow;

(3) the insulator covering a part or all of the central conductor;

(4) the external conductor covering a part or all of the insulator;

(5) the brush-like structure capable of performing microwave irradiation being connected to the central conductor directly or indirectly; and (6) the brush-like structure capable of receiving a microwave being connected to the external conductor directly or indirectly.

Note that, the hollow tube may include an aspiration tube and/or a water feed tube, and the hollow tube itself may also serve as the aspiration tube and/or the water feed tube.

The organ resection tool includes the following configuration (see FIG. 10):

(1) the central conductor having a cylindrical shape with a hollow formed therein;

(2) a hollow tube (hollow structure) formed by the hollow;

(3) the insulator covering a part or all of the central conductor;

(4) the external conductor covering a part or all of the insulator; and (5) the brush-like structure capable of performing microwave irradiation being formed by the central conductor, the insulator, and the external conductor.

(Microwave Irradiation Function of Organ Resection Tool Including Brush Structure Capable of Performing Microwave Irradiation)

The microwave irradiation function (means) of the present invention preferably includes a microwave transmission portion and a probe. The microwave transmission portion preferably includes a central conductor, an insulator, and an external conductor. The central conductor, the insulator, and the external conductor form a coaxial cable formed into a coaxial shape (see FIG. 6).

Further, the brush-like structure itself serves as a probe.

Note that, the microwave having a frequency of from 900 MHz to 6,000 MHz is equally available. The microwave having a frequency of 2,450±50 MHz is preferred.

Further, the coaxial cable used in the present invention is connected to a microwave irradiation device directly or indirectly (through intermediation of another coaxial cable).

The microwave irradiation device to be used in the present invention enables treatment with small electric power and is also excellent in safety. The electric power to be used in the present invention falls within a range of from 1 W to 100 W, preferably a range of from 5 W to 60 W, more preferably a range of from 10 W to 40 W. When the electric power is higher than 100 W, there is a risk in that the surrounding tissue may be damaged. The level of the electric power is adjusted depending on the length of an exposed portion.

(Brush-Like Structure)

The brush-like structure of the present invention is a brush-like portion for scraping off an organ (applying a pressure to living tissue), which is brought into contact with the organ (see "1" in FIG. 1).

Further, the brush-like structure of the present invention is not particularly limited as long as the brush-like structure is made of a material that has stiffness and elasticity capable of scraping off an organ and that is capable of performing microwave irradiation and/or receiving a microwave.

For example, conductive materials such as iron, copper, titanium, stainless steel, phosphor bronze, or brass can be widely used. Phosphor bronze, stainless steel, brass, etc. are preferably illustrated.

A length of one piece of the brush-like structure falls within a range of from 0.5 mm to 25 mm, a range of from 1 mm to 20 mm, or a range of from 5 mm to 15 mm. An optimum length for stiffness and elasticity in accordance with the hardness of each organ to be required for scraping off an organ (in particular, a solid organ) is selected appropriately. In the case where the brush-like structure is extremely short, the brush-like structure has a protrusion shape.

The brush-like structure includes a plurality of individual units to tens of individual units, and the individual units are ideally converged in a line. However, the individual units may spread from about 5.0 mm to about 7.0 mm in a longitudinal direction and from about 2.0 mm to about 6.0 mm in a lateral direction. As the total lateral width of the brush-like structure, 0.2 mm to 3 cm, 0.5 mm to 2.0 cm, 0.6 mm to 1.5 cm, or 0.7 mm to 11 mm are illustrated. Note that, the individual units may or may not be held in contact with each other.

Although the diameter of one piece of the brush-like structure falls within a range of from 0.1 mm to 0.5 mm, a range of from 0.2 mm to 0.5 mm, or a range of from 0.3 mm to 0.5 mm, the optimum diameter for stiffness and elasticity in accordance with the hardness of each organ to be required for scraping off a solid organ is selected appropriately.

The brush-like structure may be made of a plurality of metallic needles or may have a wire shape. Further, the brush-like structure may be branched from the central conductor or the external conductor to extend to form a brush shape.

The brush-like structure may include one or a plurality of rows of a transverse brush, a random arrangement brush, one or a plurality of rows of a circular arrangement brush, or one or a plurality of rows of a semi-circular arrangement brush.

One row of a transverse brush refers to a brush in which brush pieces are arranged laterally in a row so as to have a comb-like shape.

A plurality of rows of a transverse brush refers to a brush in which brush pieces are arranged laterally in a plurality of rows so as to have a shape in which a plurality of combs are arranged. In the case of two rows of a transverse brush, one row can be used for performing microwave irradiation, and the other can be used for receiving a microwave. Needless to say, all the rows can also be used for performing microwave irradiation or receiving a microwave. Further, in the case of a plurality of rows of a transverse brush, the respective rows can be used for performing microwave irradiation and receiving a microwave alternately. Alternatively, one or a plurality of rows of a transverse brush, in which each brush piece is used for performing microwave irradiation and receiving a microwave, can also be used.

The random arrangement brush includes brush pieces arranged at random with a predetermined width, and the brush pieces for performing microwave irradiation and the brush pieces for receiving a microwave can be arranged at random or in a predetermined combination.

One or a plurality of rows of a circular arrangement brush refers to a brush in which the above-mentioned transverse brush is formed into a circular shape, and one row of a circular arrangement brush can be used for performing microwave irradiation or receiving a microwave. In the case of a plurality of rows of a circular arrangement brush, a combination similar to that of the above-mentioned plurality of rows of a transverse brush can be used. Further, in one or a plurality of rows of a circular arrangement brush, one half of a circle can be used for performing microwave irradiation, and the other half thereof can be used for receiving a microwave.

One or a plurality of rows of a semi-circular arrangement brush refers to a brush in which the above-mentioned transverse brush is formed into a semi-circular shape, and one row of a semi-circular arrangement brush can be used for performing microwave irradiation or receiving a microwave. In the case of a plurality of rows of a semi-circular arrangement brush, a combination similar to that of the above-mentioned plurality of rows of a transverse brush can be used. Further, in one or a plurality of rows of a circular arrangement brush, one half of a semi-circle can be used for performing microwave irradiation, and the other half thereof can be used for receiving a microwave.

Each unit of the brush-like structure may be straight or curved. A tip end of the brush-like structure may be curved in an inward direction. Further, it is preferred that tip portions of the brush-like structure be aligned in a row.

The brush-like structure may be a wire having elasticity connected to the central conductor or the external conductor directly or indirectly, or may have a longitudinal needle-like structure in which the central conductor or the external conductor is formed thin. It is appropriate that a plurality of brush units be collected to form a brush shape and have an elastic force capable of abrading and crushing even a relatively hard solid organ. It is useful to converge the tips of brush units to reduce the width, because a narrow groove can be formed in cerebral surgery or the like, which makes it unnecessary to crush and coagulate an organ excessively.

Further, it is considered that the brush-like structure can also be applied as a tool (as a raspatory) for releasing organs from each other while performing hemostasis between the organs at a time of a general surgical operation.

Further, each unit of the brush-like structure may have a halved shape. When a coaxial structure including an insulating layer between a central conductor and an external conductor for performing microwave irradiation is cut in the longitudinal direction, and a plurality of extremely thin halved bodies with the central conductor exposed in the longitudinal direction are arranged in a brush shape, this arrangement can be used directly as a brush.

(Coaxial Cable)

The organ resection tool of the present invention can be inserted into an endoscope and/or a catheter by imparting flexibility to a coaxial cable. The organ resection tool preferably includes a gripping portion made of an insulator to be gripped by an operator during a surgical operation under direct vision such as a laparotomy.

The coaxial cable used in the present invention includes a central electrode of a conductor made of, for example, phosphor bronze, a shield tube of an insulator made of, for example, Teflon (trademark) covering the central electrode, and an earth pipe of an external conductor (conductor) made of, for example, brass. The outer side of the coaxial cable may be covered with a shield holder (also referred to as "guide tube"). It is preferred that the shield holder be formed of a non-conductive member (for example, Teflon (trademark), a fluorine resin, or a non-magnetic coil such as ceramics)

The preferred diameter of the coaxial body falls within a range of from 0.3 mm to 5.0 mm.

As the material for the central conductor of the coaxial body of the present invention, copper, bronze, aluminum, and the like are illustrated, and as the material for the insulator, Teflon (trademark), ceramics, and the like are illustrated. The external conductor is not particularly limited as long as the external conductor is a conductor.

(Vibration Function Means)

The brush-like structure of the present invention can also be driven in association with the vibration function means. For example, the gripping portion connected to the brush-like structure may be connected to a vibrator, specifically, may be vibrated by a portable vibrator or a stationary body.

A high-frequency transducer or an ultrasonic transducer may be used, and the transducer desirably has a frequency causing cavitation. The transducer has ultrasonic transducer for generating an ultrasonic wave and transmits the ultrasonic wave generated by the ultrasonic transducer to a target through the brush-like structure.

(Washing and Disposal Functions)

The solid organ resection tool of the present invention is preferably required to have washing and disposal functions. Therefore, means for feeding water and aspirating water is required. This means may be integrated with the solid organ resection tool or may be separated therefrom. In examples, an injection port and an aspiration port are illustrated (see FIGS. 7 to 9).

(Feature of Organ Resection Tool Including Vibration Function Means with Tip End Portion Positioned in Microwave Irradiation Range)

The organ resection tool including vibration function means with a tip end portion positioned in a microwave irradiation range according to the present invention has a feature in that the organ resection tool includes a central conductor, an external conductor, and vibration function means, and a tip end portion of the vibration function means is positioned in the microwave irradiation range.

Note that, the microwave irradiation range refers to a range (see "2" in FIG. 1) that a microwave reaches when the microwave is output from the central conductor or a probe (probe for performing microwave irradiation) connected to the central conductor directly or indirectly to the external conductor or a probe (probe for receiving a microwave) connected to the external conductor directly or indirectly. It is preferred that a surface formed of any two of the central conductor, the probe for performing microwave irradiation, the probe for receiving a microwave, and the external conductor, a space formed of any three of the central conductor, the probe for performing microwave irradiation, the probe for receiving a microwave, and the external conductor, or a space formed of all of the central conductor, the probe for performing microwave irradiation, the probe for receiving a microwave, and the external conductor can also be set to the microwave irradiation range.

Note that, the central conductor itself can serve as the probe for performing microwave irradiation, and the external conductor itself can also serve as the probe for receiving a microwave.

Further, the probe may be the same carrier as the vibration function means or may be another carrier.

Due to the above-mentioned features, the organ resection tool has the following configuration.

(1) A microwave is output from the central conductor to the external conductor, and hemostasis can be performed with the microwave while an organ is destroyed with the vibration function means.

(2) A microwave is output from the probe for performing microwave irradiation to the probe for receiving a microwave, and hemostasis can be performed with the microwave while an organ is destroyed with the vibration function means.

(3) A microwave is output from the probe for performing microwave irradiation to the external conductor, and hemostasis can be performed with the microwave while an organ is destroyed with the vibration function means.

(4) A microwave is output from the central conductor to the probe for receiving a microwave, and hemostasis can be performed with the microwave while an organ is destroyed with the vibration function means.

(Configuration of Organ Resection Tool Including Vibration Function Means with Tip End Portion Positioned in Microwave Irradiation Range)

The organ resection tool including vibration function means with a tip end portion positioned in a microwave irradiation range preferably has the following configuration but is not limited thereto. Note that, in the case where the probe and the vibration function means are provided separately from each other, the probe surrounds the tip end of the vibration function means. The shape of the probe is not particularly limited and may be a ring shape or a horn shape as long as the probe surrounds the vibration function means.

Figure 11:
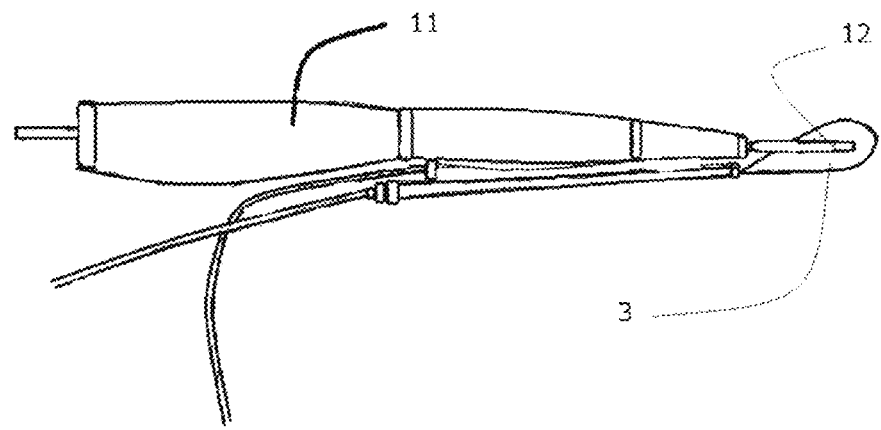
FIG. 11 is an entire view of an organ resection tool including vibration function means with a tip end portion positioned in a microwave irradiation range.

(1) An organ resection tool in which a central conductor and an external conductor form a ring shape through intermediation of an insulator, and a tip end portion of vibration function means is positioned in a microwave irradiation range defined by the ring (see FIG. 11).

Figure 14:
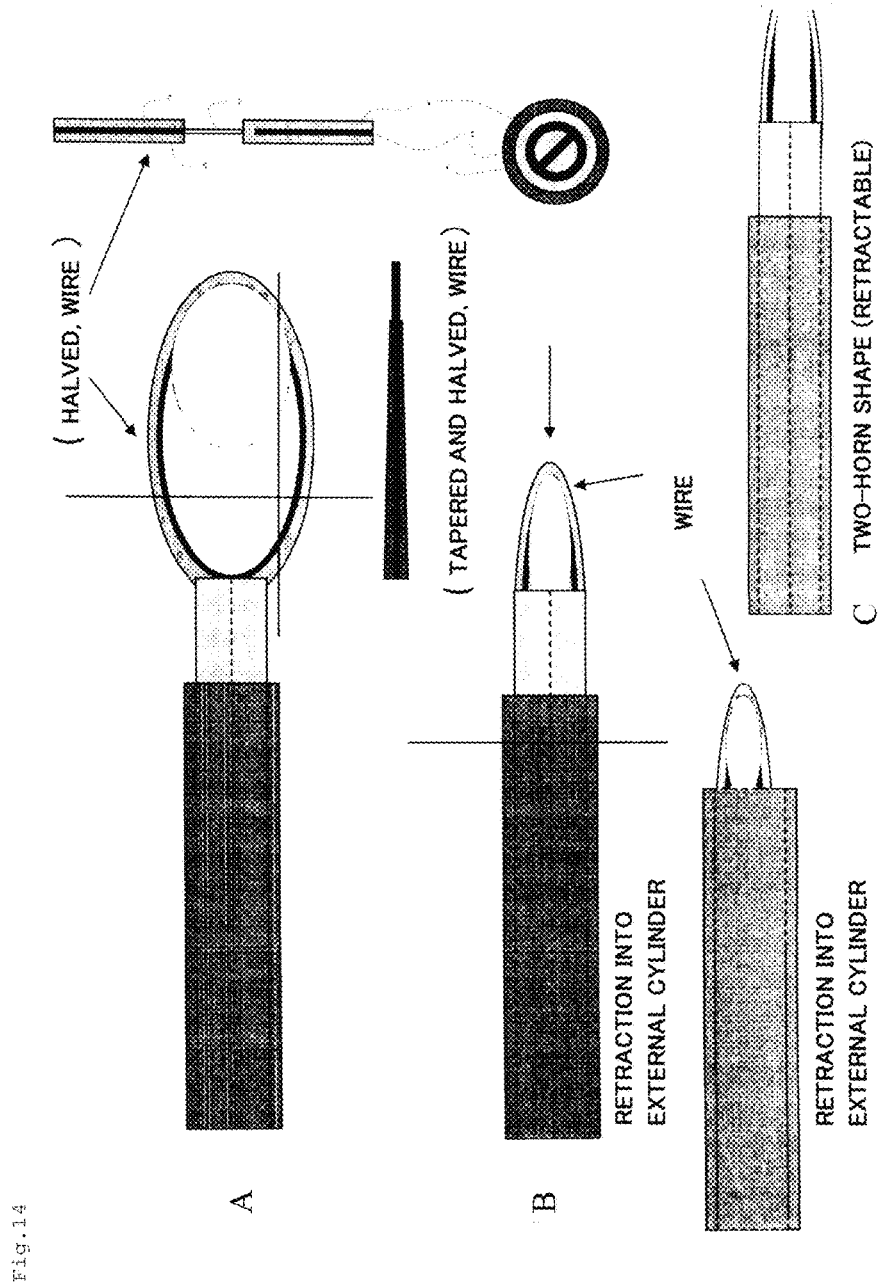
FIG. 14 are views each illustrating a form in which a probe of the organ resection tool including vibration function means with a tip end portion positioned in a microwave irradiation range is formed into a wire ring.

(2) An organ resection tool in which a coaxial structure including an insulator (insulating layer) between a central conductor and an external conductor is cut in the longitudinal direction to form a halved shape (wire ring shape) with the central conductor exposed in the longitudinal direction, and a tip end portion of vibration function means is positioned in a microwave irradiation range defined by the ring (see FIG. 14A).

(3) An organ resection tool in which a central conductor and an external conductor have bar-like or needle-like structures, respectively, which are formed independently from each other, and a tip end portion of vibration function means is positioned in a microwave irradiation range defined by the central conductor and the external conductor (see FIG. 14C). Further, an organ resection tool in which a coaxial structure including an insulating layer between a central conductor and an external conductor is cut in the longitudinal direction to form a halved shape with the central conductor exposed in the longitudinal direction, and a tip end portion of vibration function means is positioned in a microwave irradiation range defined by the central conductor and the external conductor.

(4) An organ resection tool including a cylindrical central conductor, an insulator covering a part or all of the central conductor, an external conductor covering a part or all of the insulator, and vibration function means, in which the central conductor is exposed in a longitudinal axis direction without being partly covered with the insulator and the external conductor, and a tip end portion of the vibration function means is positioned in a microwave irradiation range defined by the exposed central conductor and the external conductor.

(5) An organ resection tool including a central conductor having a cylindrical shape with a hollow formed therein, a hollow tube (hollow structure) formed by the hollow, an insulator covering a part or all of the central conductor, an external conductor covering a part or all of the insulator, and vibration function means, in which the brush-like structure capable of performing microwave irradiation is formed by the central conductor, the insulator, and the external conductor, and a tip end of the vibration function means is positioned in a microwave irradiation range defined by the exposed central conductor and the external conductor.

In the case where the probe and the vibration function means are identical, the probe is provided with a vibration function. The shape of the probe is not particularly limited similarly and is preferably a ring shape or a horn shape.

In the case where the probe is a horn-shaped body, when the horn-shaped body has one horn, the probe having the above-mentioned halved structure is provided with vibration function means. Even when the horn-shaped body has two or more horns, a plurality of horn-shaped bodies may be halved, and each halved structure or at least one halved structure may be provided with vibration function means. Alternatively, one of two horns may be defined as a central conductor and the other is defined as an external conductor, and both or one of the conductors, preferably, both of the conductors may be provided with vibration function means. In the case of three horns, a central conductor is set at the center and external conductors are set at both sides, or an external conductor is set at the center and central conductors are set at both sides, and at least one horn, preferably, three horns, two horns at both sides, or one horn at the center may be provided with vibration function means. In the case of four horns, a set of a central conductor and an external conductor is provided to each of both right and left sides of the four horns, and at least one horn, preferably, four horns, two horns at both side ends, or two horns at the center may be provided with vibration function means.

(Microwave Irradiation Function of Organ Resection Tool Including Vibration Function Means with Tip End Portion Positioned in Microwave Irradiation Range)

The microwave irradiation function (means) of the present invention preferably includes a microwave transmission portion and a probe. The microwave transmission portion preferably includes a central conductor, an insulator, and an external conductor. The central conductor, the insulator, and the external conductor form a coaxial cable formed into a coaxial shape (see FIG. 6).

Note that, the microwave having a frequency of from 900 MHz to 6,000 MHz is equally available. The microwave having a frequency of 2,450±50 MHz is preferred.

Further, the coaxial cable used in the present invention is connected to a microwave irradiation device directly or indirectly (through intermediation of another coaxial cable).

The microwave irradiation device to be used in the present invention enables treatment with small electric power and is also excellent in safety. The electric power to be used in the present invention falls within a range of from 1 W to 100 W, preferably a range of from 5 W to 60 W, more preferably a range of from 10 W to 40 W. When the electric power is higher than 100 W, there is a risk in that the surrounding tissue may be damaged. The level of the electric power is adjusted depending on the length of an exposed portion.

The probe is preferably connected to the tip end of the microwave transmission portion directly or indirectly. The cross-sectional area of the probe is smaller than that of a coaxial cable connection portion. The probe is connected to the central conductor or integrally formed therewith.

It is preferred that a part or all of the central conductor be covered with the insulator, a part or all of the insulator be covered with the external conductor, and the ratio between the cross-sectional area of the central conductor and that of the external conductor be kept constant. As long as the ratio is kept constant, the cross-sectional areas may become smaller gradually or in stages. The thinned tip end portion of the tapered coaxial body includes a coaxial body keeping a predetermined diameter.

Note that, the shapes of the cross sections of the central conductor and the external conductor are not particularly limited, and may be a circular shape, a fan shape, a rectangular shape, a triangular shape, or the like, preferably, a circular shape.

In addition, the cross-sectional area of the external conductor generally means the difference between the cross-sectional area of the coaxial cable and the cross-sectional area of the central conductor and the insulator.

The ratio of the circular diameter of the central conductor to the circular inner diameter of the external conductor preferably falls within a range of from 0.2 to 0.4, more preferably a range of from 0.22 to 0.3. Note that, in the case where the central conductor and the external conductor are independent from each other, the diameters of both may be the same.

In the case where the probe is not integrally formed with the vibration function means, the length of the probe is preferably required to be at least the length surrounding the vibration function means, and the length from a root portion of the probe to the tip end portion thereof falls within a range of from 1.0 mm to 80 mm, more preferably a range of from 5.0 mm to 60 mm, still more preferably a range of from 10 mm to 40 mm. Needless to say, the probe may be a ring in general, and in the case where the probe is a ring, the length of the probe may be substantially twice as large as that of the ring.

The diameter of the coaxial cable connection portion of the probe is substantially the same as the diameter of the coaxial cable. The diameter of the tip end of the probe falls within a range of from 0.2 mm to 5 mm, preferably a range of from 0.3 mm to 3 mm, more preferably a range of from 0.3 mm to 2 mm. It is preferred that the probe maintain at least elasticity.

The probe includes a living tissue contact portion. In a ring-like probe, the insulator is positioned between the central conductor and the external conductor. In a halved ring-like probe, the living tissue contact portion includes a central conductor exposed linearly, an insulator on each side of the central conductor, and an external conductor on an outer side of the insulator. In a two-horn probe, the living tissue contact portion is exposed as the central conductor and the external conductor separately. Alternatively, in a halved horn-shaped probe, the living tissue contact portion includes a central conductor exposed linearly in a longitudinal axis direction, an insulator on each side of the central conductor, and an external conductor on an outer side of the insulator.

(Vibration Function Means of Organ Resection Tool Including Vibration Function Means with Tip End Portion Positioned in Microwave Irradiation Range)

The vibration function means of the present invention may be the same carrier as the probe or may be another carrier. The carrier is connected to the vibrator, specifically, may be vibrated by a portable vibrator or a stationary body. An ultrasonic transducer may be used, and the transducer desirably has a frequency causing cavitation. The transducer preferably includes an ultrasonic transducer for generating an ultrasonic wave and a transmission member for transmitting the ultrasonic wave generated by the ultrasonic transducer to a target.

(Ultrasonic Transducer)

The ultrasonic transducer has a structure in which a piezoelectric material such as PZT is interposed between electrodes, and the piezoelectric material is subjected to expansion and contraction drive to generate ultrasonic vibration when a current is applied. The ultrasonic transducer is connected to an oscillator. As the ultrasonic transducer, any of a Langevin transducer in which the transducers are fixed in a laminated state to a casing serving as a transmission member with bolts, and an adhesive transducer fixed with an adhesive can be applied. The frequency of an ultrasonic wave generated by the ultrasonic transducer falls within a range of from 0.10 MHz to 80 MHz, more preferably a range of from 1.0 MHz to 40 MHz. Alternatively, the frequency may be 16 Hz to $2 \times 10^4$ Hz. Further, the output of an ultrasonic wave preferably falls within a range of from 0.1 W to 200 W, more preferably a range of from 1.0 W to 50 W for the following reasons. When the frequency is lower than 0.10 MHz, cavitation air bubbles become larger, and cells become liable to be destroyed due to the impact caused by the crushing of the cavitation air bubbles. When the frequency is higher than 20 MHz, the generation of cavitation becomes less likely to occur. Further, when the output is lower than 0.1 W, the generation of cavitation becomes difficult. An ultrasonic transducer for generating an ultrasonic wave larger than 200 W may be used to annihilate cells with the energy and sound pressure. The ultrasonic wave to be released is not limited to a continuous wave and may be a pulse wave. In the case of a pulse wave, for example, it is appropriate to control the following procedure to be repeated, which involves releasing an ultrasonic wave having a certain output and a certain frequency for 10 seconds, and then, suspending the release of an ultrasonic wave for 10 seconds.

(Casing)

The casing serving as the transmission member has a substantially cap shape, and an ultrasonic wave irradiation surface is formed on the surface thereof. Although the material for forming the casing is not particularly limited, the casing is formed of, for example, a metallic material such as aluminum or stainless steel. It is preferred that the casing be covered with an insulator. It is preferred that, in order to bring the ultrasonic irradiation surface and a target into close contact with each other, gel or the like be applied therebetween. An ultrasonic wave absorption member for suppressing the vibration transmission of an ultrasonic wave can also be provided on a side surface of the casing. The purpose is to irradiate only an intended target with an ultrasonic wave and prevent other parts from being erroneously irradiated with the ultrasonic wave by causing the ultrasonic wave to be released only from the ultrasonic wave irradiation surface on the upper surface of the casing. The ultrasonic absorption member can be formed of a material having a resin, sponge, or an air layer that does not transmit the vibration of an ultrasonic wave, and any material can be applied to the ultrasonic absorption member as long as the material is capable of suppressing the vibration transmission of an ultrasonic wave. The ultrasonic absorption member can be mounted on a side surface of the casing by winding a protecting material for suppressing the vibration transmission of an ultrasonic wave around the casing, applying the protective material to the side surface, or causing the protective material to adhere to the side surface. A cooling tube or the like can also be wound around the outer periphery of the casing.

In the vibration function means, the living tissue contact portion is substantially the above-mentioned transmission member. In the case where the transmission member has a bar shape, the transmission member has a length of from about 5 mm to about 30 mm and a diameter of from 5 mm to 20 mm. The total length of the transducer falls within a range of from about 20 mm to about 70 mm. The diameter of the transducer falls within a range of from 5 mm to 20 mm. In the case where the transmission member is the same carrier as microwave irradiation probe function means, the living tissue contact portion has both the functions, that is, the transmission member also serves as a probe. In the case where the transmission member has a bar shape, the above-mentioned dimensions are adopted. However, in the case where the transmission member has a ring shape, an elastic ring is used as the transmission member, and the transmission member is caused to exhibit a microwave irradiation probe function. Therefore, the diameter in this case is preferably 3 mm to 20 mm in accordance with the above-mentioned definition of the probe.

Further, it is required that the vibration function means substantially have washing and disposal functions. For this purpose, means for feeding water and aspirating water is required. This means may be integrated with the vibration function means or may be separated therefrom. In examples, this means is illustrated as a water injection tube and an aspiration cannula.

The organ resection tool of the present invention is hereinafter descried in detail by way of specific examples. Note that, the present invention is not limited to the examples.

Example 1

(Organ Resection Tool Including Brush Structure Capable of Performing Microwave Irradiation)

Embodiments of the organ resection tool including a brush structure capable of performing microwave irradiation are hereinafter described.

First Embodiment

Figure 2A:
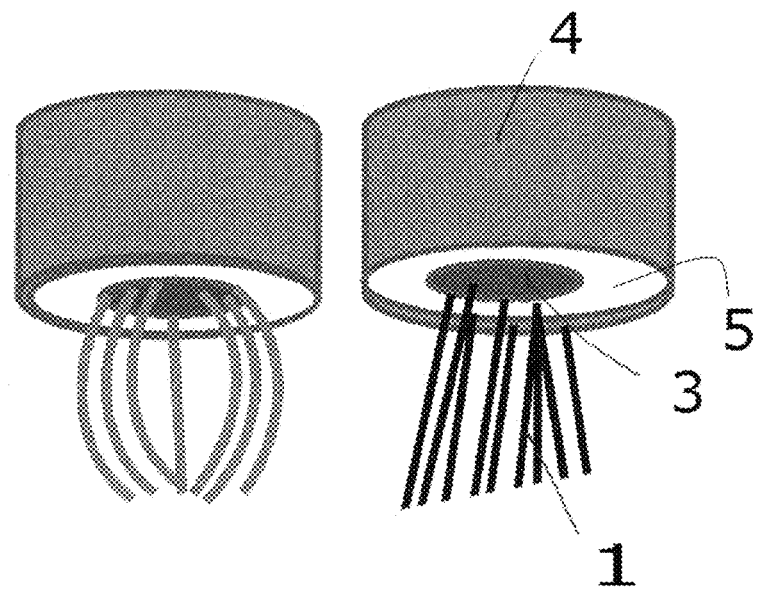
FIG. 2A is an oblique view of a tip end of the organ resection tool including a brush structure capable of performing microwave irradiation.
Figure 2B:
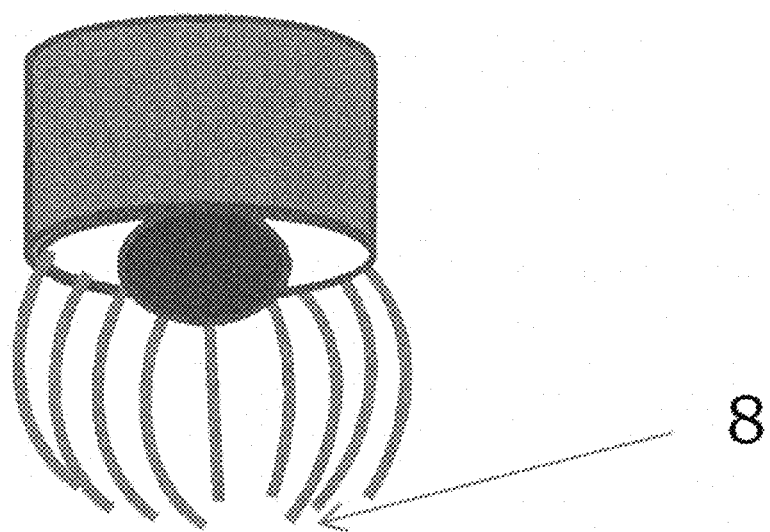
FIG. 2B illustrates a state in which a brush structure having a needle-like structure of the organ resection tool including a brush structure capable of performing microwave irradiation is branched from a central conductor.
Figure 3:
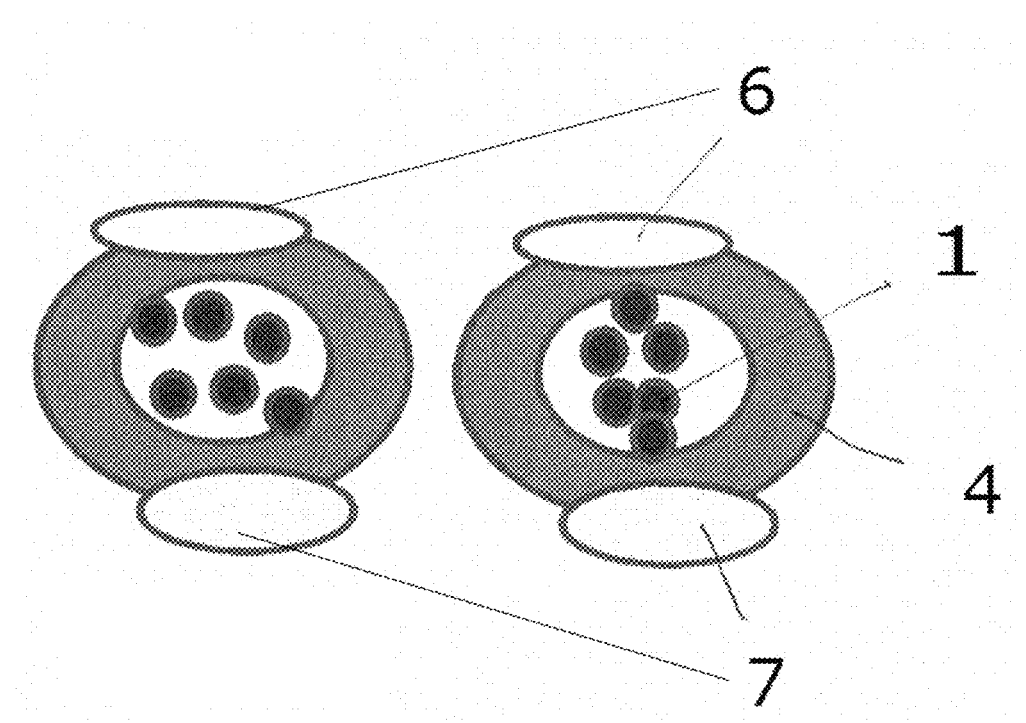
FIG. 3 is a sectional view of the organ resection tool including a brush structure capable of performing microwave irradiation.

FIGS. 1 to 3 illustrate an embodiment of the organ resection tool including a brush structure capable of performing microwave irradiation according to the present invention.

The organ resection tool of the present invention includes a brush-like structure (1) prepared with phosphor bronze, and the brush-like structure is connected to a central conductor (3). An external conductor (4) covers the central conductor (3) through intermediation of an insulator (5). A microwave from a microwave oscillator is radiated from the brush-like structure.

The brush-like structure (1) serves as a microwave irradiation device (means) having a metallic brush-like structure branched from the central conductor (3). Alternatively, the brush-like structure may receive a microwave from the metallic brush-like structure branched from the external conductor (4).

Further, a range that a microwave reaches (2: microwave irradiation range) is illustrated in the organ resection tool on the right side of FIG. 1.

When the organ resection tool is used, the brush-like structure (1) scrapes off tissue of an organ (liver). While the liver tissue is being scraped off, a microwave is radiated from the brush-like structure itself to perform bleeding from the surrounding tissue of the liver tissue.

In addition, the organ resection tool may include a water injection tube (6: water feed tube) and an aspiration tube (7) for washing and aspirating a crushed cell fragment concurrently with the scraping-off and hemostasis of the tissue (FIG. 3). With this, the brush-like structure (1) can be prevented from being heated by microwave irradiation, and a microwave can be radiated continuously. In addition, the bleeding amount is minimized, and a bottom portion of a wound in a line to be cut open can be set visible constantly.

Second Embodiment

Figure 4:
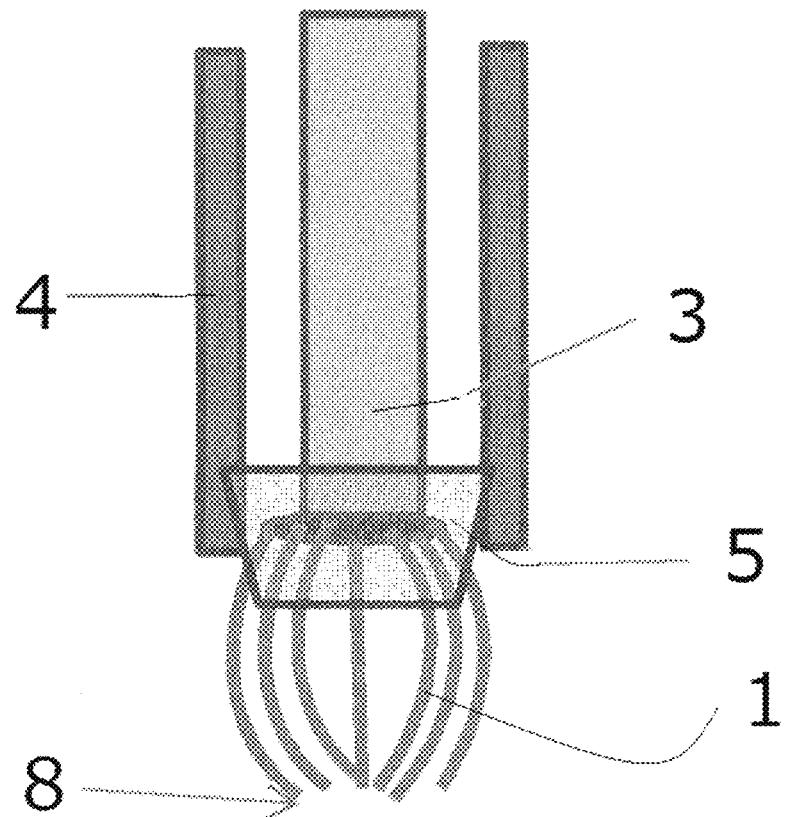
FIG. 4 is a side sectional view of the organ resection tool including a brush structure capable of performing microwave irradiation.

The material for a brush of the brush-like structure (1) is a stainless elastic metal, which is a conductor for transmitting a microwave. The brush-like structure (1) is connected to the central conductor (3) or the external conductor (4). Note that, the brush-like structure (1) having a needle-like structure has an elastic force for abrading out relatively hard tissue and returns to the original form. The tip ends of pieces of the brush-like structure (1) may or may not be held in contact with each other (FIGS. 2-2 and 4). Note that, "8" in FIG. 2-2 denotes a site with which the tissue is brought into contact.

Third Embodiment

The organ resection tool has a structure in which water is injected to tissue dissected with the metallic brush-like structure (1) from the water feed tube (6), and on the other hand, the water containing the tissue that has been scraped off is aspirated from the aspiration tube (7) (FIG. 3).

The diameter of each unit of the brush-like structure (1) is prepared so as to fall within a range of from 0.1 mm to 0.01 mm, and the length of each unit of the brush-like structure is prepared so as to fall within a range of from 5.0 mm to 20 mm.

A plurality of units of the brush-like structure (1) form a brush-like structure. A needle of one brush unit of the brush-like structure (1) may be a wire structure or a central conductor. Further, the respective metallic needles have a structure in which no electricity is charged when the metallic needles are brought into contact with each other.

Fourth Embodiment

The function of vibrating the brush-like structure (1) (vibration function means capable of vibrating a brush-like structure) may be provided through connection with a high-frequency generator or an ultrasonic generator (not shown).

Fifth Embodiment

The brush-like structure (1) may have a straight shape or a loop shape (FIG. 2). The straight shape is illustrated in FIG. 1 or the right side of FIG. 2, in which the brush tip portions of the brush-like structure (1) are aligned in a row.

In the case where the brush-like structure (1) has a loop shape, the brush-like structure (1) is curved in an inward direction at a tip end (left of FIG. 2). Further, the brush-like structure (1) may be branched from the central conductor (3) (FIG. 2). The brush-like structure (1) is connected to the central conductor (3), and the external conductor (4) surrounds the central conductor (3) except for the brush-like structure (1). The external conductor (4) is partitioned from the brush-like structure (1) and the central conductor (3) through intermediation of the insulator (5) or via an air gap (FIG. 4).

Sixth Embodiment

Figure 5:
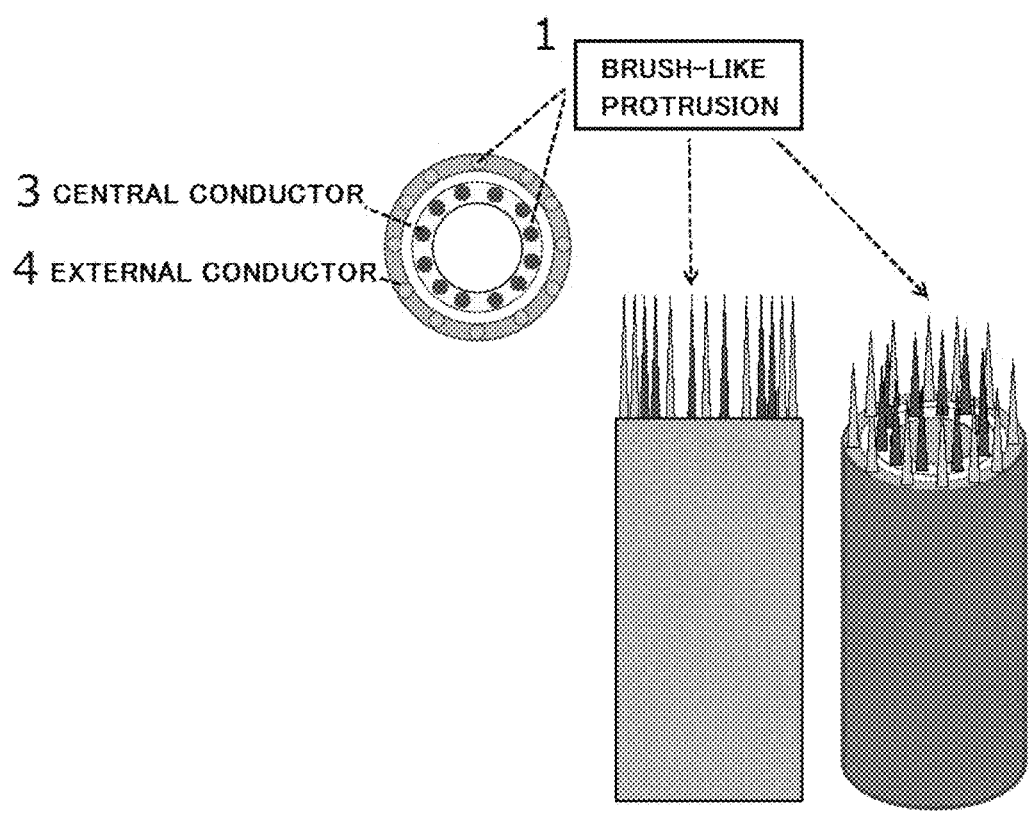
FIG. 5 is a view illustrating a form in which the brush-like structure of the organ resection tool including a brush structure capable of performing microwave irradiation has a double circular arrangement.

The brush-like structure (1) is arranged in two circles, and for example, an outside circle is defined as a microwave receiver connected to the external conductor (4), and an inside circle is defined as microwave irradiation means connected to the central conductor (3) (FIG. 5).

The left side of FIG. 5 is a tip end view of the organ resection tool, and the center of FIG. 5 is a lateral view thereof. The right side of FIG. 5 is a perspective top view of the organ resection tool. Each brush piece is connected to the central conductor (3) or the external conductor (4).

Figure 6:
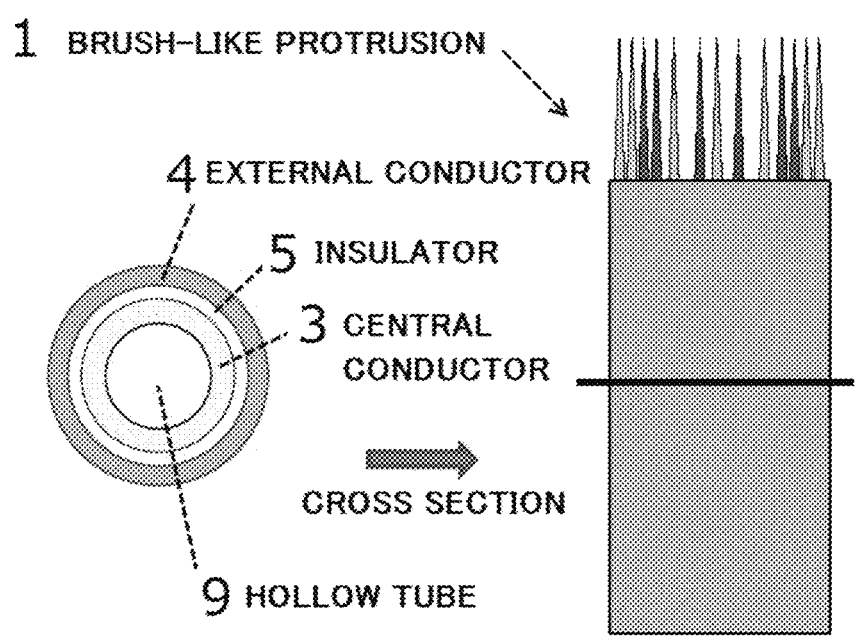
FIG. 6 is a view illustrating an internal structure of a handle portion in the form in which the brush-like structure of the organ resection tool including a brush structure capable of performing microwave irradiation has a double circular arrangement.

FIG. 6 illustrates a three-dimensional structure of a handle portion serving as a handgrip for an operation, which is connected to the brush-like structure (1). The left side of FIG. 6 corresponds to a sectional view of a center portion of the right side of FIG. 6. The handle portion is formed of a hollow tube (9), a central conductor (3), an insulator (5), and an external conductor (4).

Figure 7:
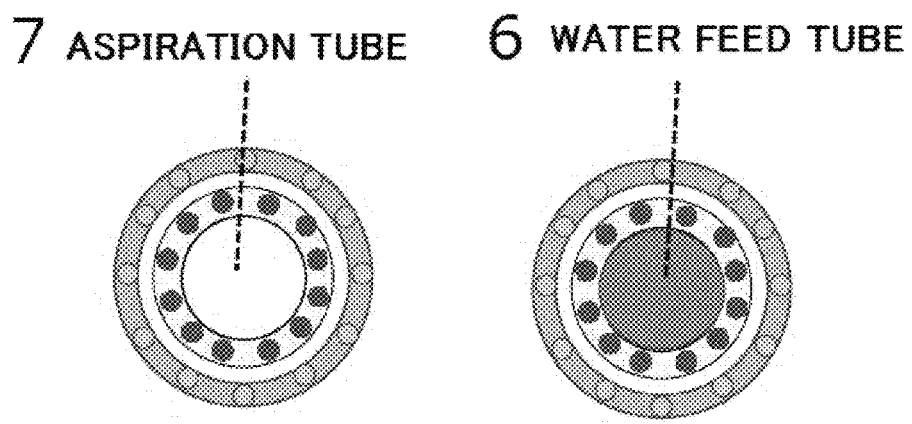
FIG. 7 is a view illustrating a manner of water feeding and aspiration of the organ resection tool including a brush structure capable of performing microwave irradiation.

Further, FIG. 7 illustrates a manner of water feeding and water aspiration. The hollow tube (9) serves as the aspiration tube (7) and/or the water feed tube (6).

Figure 8:
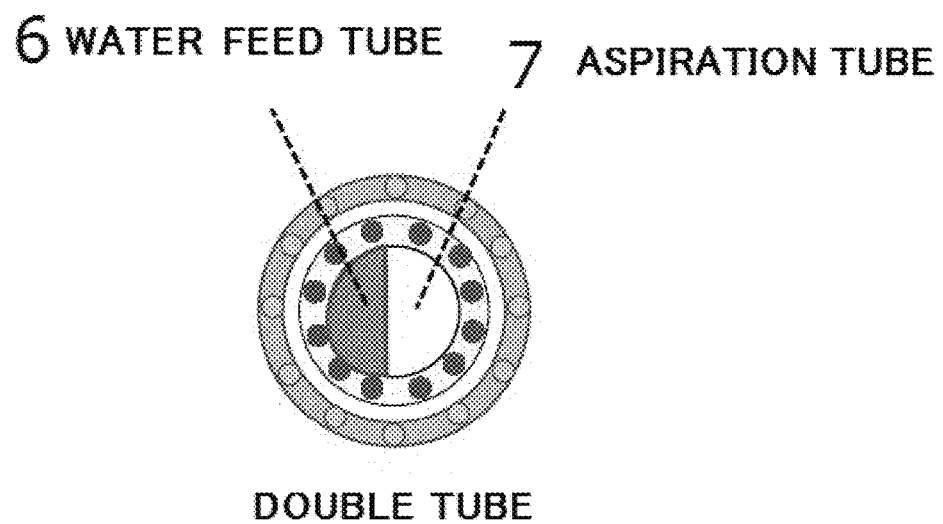
FIG. 8 is a view illustrating a manner of water feeding and aspiration of the organ resection tool including a brush structure capable of performing microwave irradiation.

FIG. 8 illustrates the case where the hollow tube (9) is halved, and one half is defined as the aspiration tube (7) and the other is defined as the water feed tube (6).

Figure 9:
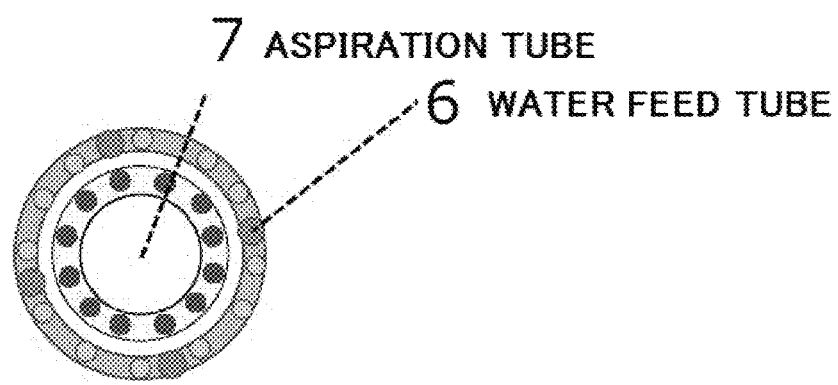
FIG. 9 is a view illustrating a manner of water feeding and aspiration of the organ resection tool including a brush structure capable of performing microwave irradiation.

FIG. 9 illustrates the case where the water feed tube (6) passes through a part of an outer circular portion, and the hollow tube (9) is used as the aspiration tube (7).

Seventh Embodiment

Figure 10:
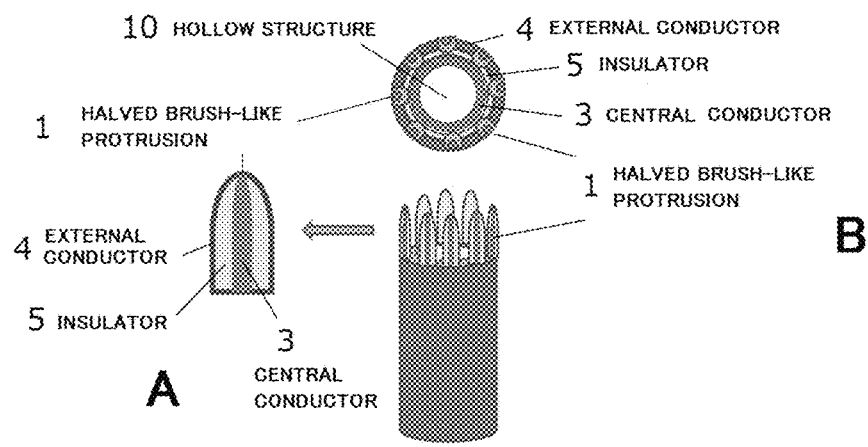
FIG. 10 is a view illustrating a form of a brush-like structure having a halved structure of the organ resection tool including a brush structure capable of performing microwave irradiation.

FIG. 10 illustrates a form in which each unit of the brush-like structure (1) has a halved structure.

Each unit of the brush-like structure (1) is arranged so as to be combined with the central conductor (3), the insulator (5), and the external conductor (4). Specifically, in the brush-like structure (1), the central conductor (3), the insulator (5), and the external conductor (4) are exposed. Such a halved brush-like structure (1) is arranged in a circular shape, and needless to say, the halved brush-like structure (1) may be a semi-circular arrangement, an oval arrangement, a one-row arrangement, or a multi-row arrangement.

FIG. 10A is a lateral view of one unit of the brush-like structure (1).

FIG. 10B is a view of a tip end of the organ resection tool, in which the hollow structure (10) is provided at the center, and the handgrip portion has a columnar structure including the central conductor (3), the insulator (5), and the external conductor (4) in the stated order from the inner side, and is connected to each of the central conductor (3), the insulator (5), and the external conductor (4) of the brush-like structure (1).

Application Example 1: Liver Excision

The brush of the brush structure capable of performing microwave irradiation according to the present invention is moved back and forth while being brought into contact with the cirrhotic liver along a general position at which the liver is cut, and the liver surface is dissected with the brush to scrape away the liver parenchyma. Concurrently, the liver surface is irradiated with a microwave from the brush-like structure, and the dissected portion is coagulated and subjected to hemostasis, with the result that the liver surface can be formed into a groove without bleeding. Although minute blood vessels are cut by being dissected, the bleeding therefrom can be stopped. Thus, a groove is formed with the brush along a preset excision line, with the result that the liver is resected.

The same treatment can be performed even in cerebral surgery and a pancreas operation. In particular, the tissue is hard in the cirrhotic liver and cannot be handled with a general surgical tool. However, the brush structure capable of performing microwave irradiation according to the present invention enables, for the first time, coagulation of tissue and aspiration of cut tissue, and can also be used for a surgical operation of the cirrhotic liver.

Application Example 2: Gallbladder is Removed from Liver Bed

In the case where the gallbladder is removed from the liver bed, the tissue between the organs is not dense, and hence the tissue is opened slightly if the gallbladder and the liver bed are pulled. However, bleeding cannot be avoided due to the presence of capillary blood vessels.

However, the brush of the brush structure capable of performing microwave irradiation according to the present invention is brought into contact with the tissue and applies tension to the organs to the right and left, with the result that the gallbladder is excised with the brush or dissected along a releasing surface. With this, the fine blood vessels are subjected to releasing and resecting operations while hemostasis is being performed, and the organs can be released from each other.

Unlike the related-art sharp releasing with a blade, the brush structure capable of performing microwave irradiation according to the present invention does not cause cutting failure (cutting of one organ), and can perform resecting and releasing without damaging the organs with which the brush structure is brought into contact.

Example 2

(Organ Resection Tool Including Vibration Function Means with Tip End Portion Positioned in Microwave Irradiation Range)

Embodiments of an organ resection tool including vibration function means with a tip end portion positioned in a microwave irradiation range are hereinafter described. An organ resection tool including both a probe and vibration function means is hereinafter described. Note that, although an organ resection tool is disclosed in which a probe and vibration function means are provided separately, in the case where the probe is defined as the same carrier as the vibration function means, the vibration function means is connected to the probe.

First Embodiment

Figure 12:
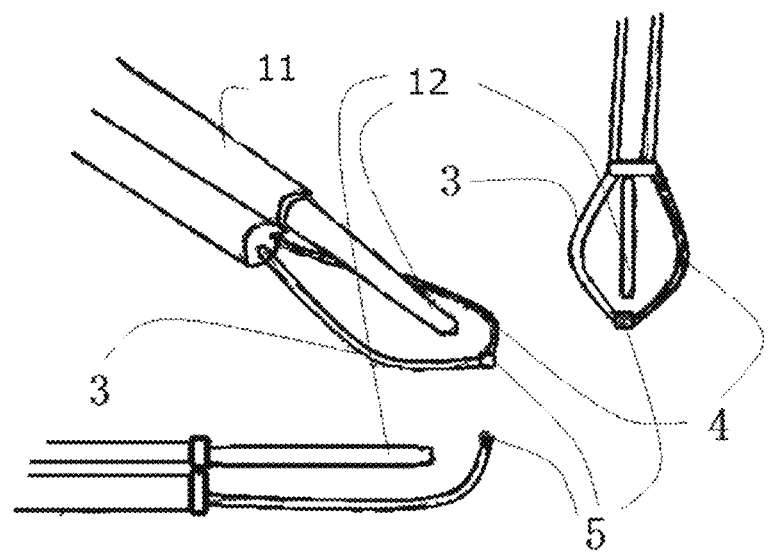
FIG. 12 is a view of the organ resection tool including vibration function means with a tip end portion positioned in a microwave irradiation range, when viewed from a diagonal direction, a lateral direction, and from the top.

As the transducer (12) serving as the vibration function means of the organ resection tool including vibration function means with a tip end portion positioned in a microwave irradiation range according to the present invention, a commercially available cavitron ultrasound surgical aspirator (CUSA) was used, and a ring-like probe was set so as to surround the tip end of the transducer (FIGS. 11 and 12). The surrounded portion serves as a microwave irradiation range.

The liver of a pig was cut with an ultrasonic output of from 40 W to 60 W of the transducer (12). In this case, the liver was cut with the CUSA, and concurrently, the microwave was radiated to the microwave irradiation range surrounding the transducer (12) to stop bleeding from tissue in the range. It is preferred that the organ resection tool include the water feed tube (6) and the aspiration tube (7) for washing and aspirating the crushed cell fragment concurrently with the stop of hemostasis. With this, the microwave irradiation can be prevented from heating the probe, and the irradiation of the microwave can be continued. In addition, the bleeding amount is minimized, and a bottom portion of a wound in a line to be cut open can be set visible constantly.

Second Embodiment

A two-horn probe was arranged so as to sandwich the transducer (12) at a distance of 2 mm from the transducer (12). Concurrently with the operation of the transducer (12), a microwave was radiated from the probe positioned on both sides of the transducer (12), with the result that bleeding from the surrounding tissue was stopped. Accordingly, the same effects as those of Example 1 were obtained.

Third Embodiment

One of two horns of a two-horn probe was connected to the central conductor (3), and the other was connected to the external conductor (4). The probe was set so as to sandwich the transducer (12) at a distance of 2 mm from the transducer (12). Concurrently with the operation of the transducer (12), a microwave was radiated from the central conductor (3), with the result that bleeding from the surrounding tissue was stopped. Accordingly, the same effects as those of Example 1 were obtained.

Fourth Embodiment

A one-horn probe was integrated with the transducer (12). Concurrently with the operation of the transducer (12), a microwave was radiated from the probe, with the result that bleeding from the surrounding tissue was stopped. Accordingly, the same effects as those of Example 1 were obtained.

Fifth Embodiment

The tip end of the transducer (12) connected to a vibrating body (11) is adjusted so as to have the same height as that of a loop-like probe (FIG. 12). The loop-like probe is connected to a microwave irradiation device through a coaxial cable.

The transducer (12) is connected to an ultrasonic generation device (vibrating body (11)). One half of the loop-like probe serves as the central conductor (3), and the other corresponding half serves as the external conductor (4). The central conductor (3) and the external conductor (4) are derived from a root portion separately to form a loop and are connected to each other through intermediation of the insulator (5) in the tip end portion (FIG. 12).

Sixth Embodiment

The vibrating body (11) is connected to the loop-like probe of the fifth embodiment to form the probe also having a vibration function. In the case of this form, the diameter of the probe is set to 3 mm so as to reinforce the elasticity of the probe.

Seventh Embodiment

Figure 13A:
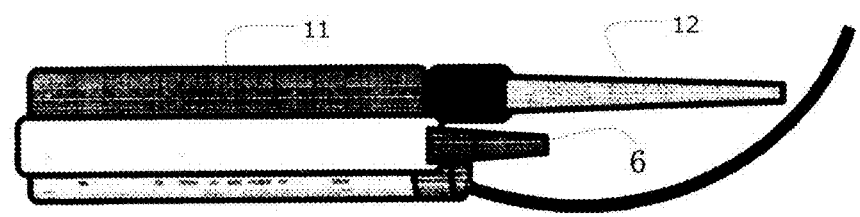
FIG. 13A is a view of the organ resection tool including vibration function means with a tip end portion positioned in a microwave irradiation range, when viewed from a lateral direction.
Figure 13B:
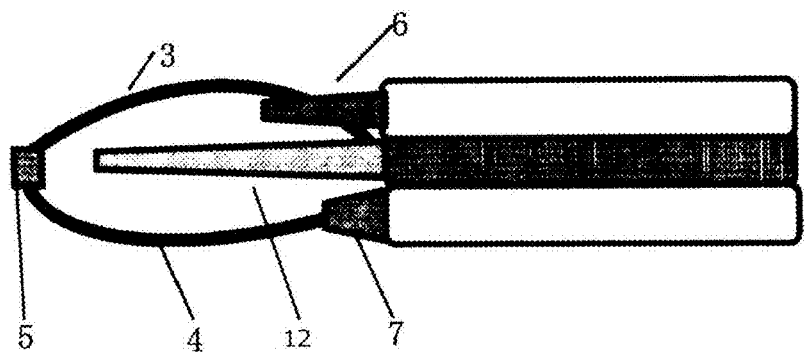
FIG. 13B is a view of the organ resection tool including vibration function means with a tip end portion positioned in a microwave irradiation range, when viewed from the top.
Figure 13C:
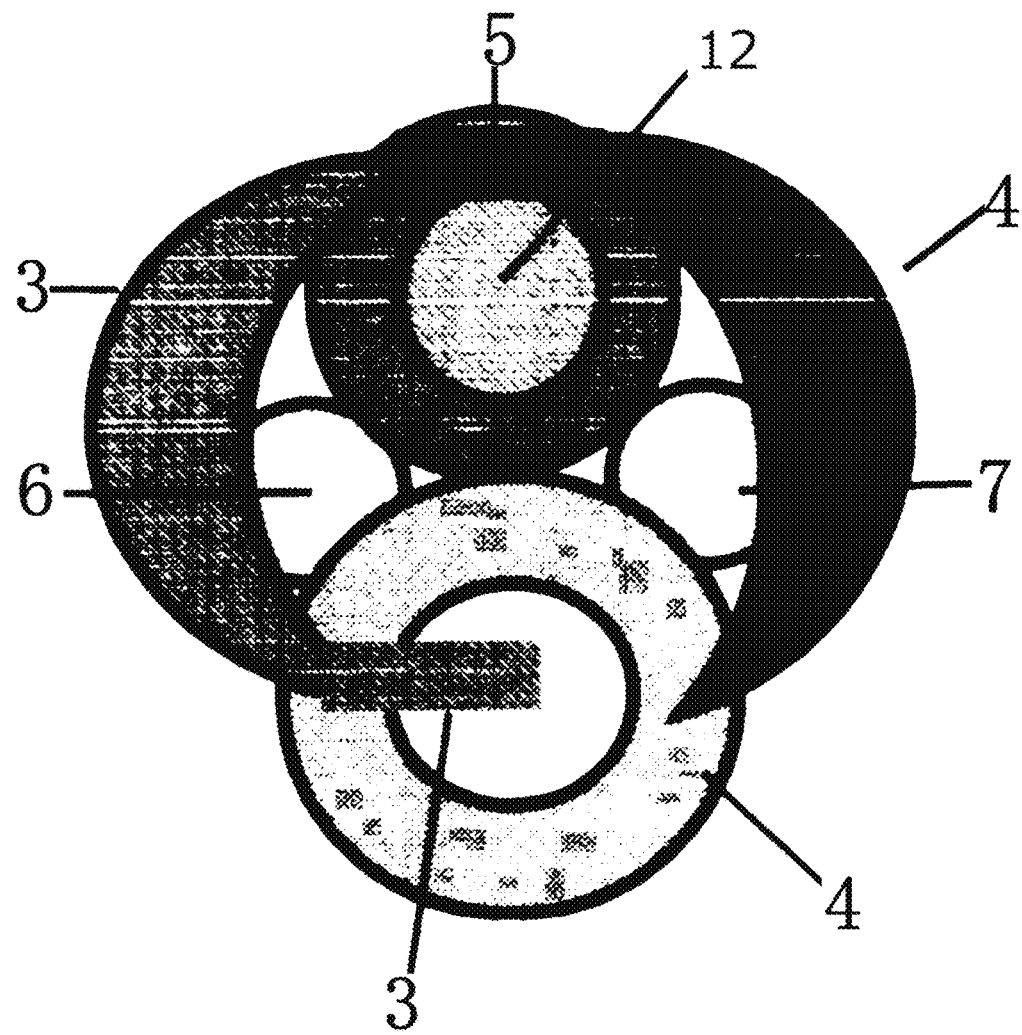
FIG. 13C is a view of the organ resection tool including vibration function means with a tip end portion positioned in a microwave irradiation range, when viewed from a tip end (front) of the organ resection tool.

FIGS. 13A to 13C illustrate embodiments of the organ resection tool of the fifth embodiment including the water feed tube (6) and the aspiration tube (7).

FIG. 13A is a view of the organ resection tool when viewed from a lateral direction, in which the vibrating body (11) and the transducer (12) are provided and a probe extends from the bottom so as to surround the transducer (12). The water feed tube (6) is positioned between the probe and the transducer.

FIG. 13B is a view of the organ resection tool when viewed from the top, in which the loop-like probe formed of the central conductor (3) and the external conductor (4) through intermediation of the insulator (5) surrounds the transducer (12). The water feed tube (6) and the aspiration tube (7) are set in addition to the probe and the transducer (12) and used for washing away the tissue.

FIG. 13C is a view of the organ resection tool when viewed from the tip end (when viewed in a panoramic way from the front side), in which a three-dimensional relationship of respective components can be confirmed. The transducer (12) and the tissue adhesion surface of the probe are positioned at the same height.

Eighth Embodiment

FIG. 14A illustrates a probe formed of a wire ring in which the central conductor (3) is exposed along the loop shape, and the tip end of the ring serves as only the external conductor (4). The insulator (5) is present on both sides of the central conductor (3), and the external conductor (4) is set on both the outer sides of the insulator (5).

FIG. 14B illustrates a form in which a probe can be retracted into an external cylinder.

FIG. 14C illustrates a form in which a two-horn probe can be retracted into an external cylinder.

Ninth Embodiment

A coaxial body is produced, for example, as follows.

A central conductor is formed by spray forming through use of a metal injection mold (MIM). Then, an electric insulation substance such as ceramics or a fluorine resin is applied to the circumferential surface of the central conductor. Alternatively, a ceramic injection mold (CIM) may be used. An insulating layer can also be formed by coating, drying, and sintering. Further, an external conductor is formed on the upper surface of the insulating layer, for example, through MIM. The tip end portion of the coaxial body is ground with a turning machine or a grinding wheel to form a probe (or a brush structure). The coaxial body is connected to a microwave transmission portion electrically or mechanically. The coaxial body may be fixed to the microwave transmission portion or may be removably connected thereto. In a GHz band, a fluctuation in impedance caused by the connection can be matched with a circuit.

INDUSTRIAL APPLICABILITY

The organ resection tool including a brush structure capable of performing microwave irradiation according to the present invention serves as an organ coagulation cutter or a raspatory based on the strong hemostasis effect irrespective of a simple structure that has not been obtained in the related art. Further, the structure thereof becomes simple, lightweight, and inexpensive.

The organ resection tool of the present invention can also be used for the excision of a fine solid organ, which cannot be achieved with a related-art surgical tool. On the other hand, the organ resection tool of the present invention can also dissect a solid organ that is so hard and cannot be excavated with a related-art ultrasonic aspiration device.

The organ resection tool including vibration function means with a tip end portion positioned in a microwave irradiation range according to the present invention achieves the following effects. Tissue of a surface with which a transducer is brought into contact is crushed and bleeds slightly, but a probe stops bleeding from the tissue of the surface. Therefore, the crushed surface is fixed with the bleeding stopped, and the bleeding from capillary blood vessels is prevented. Further, the amount of slight bleeding is small, with the result that the surgical operation field becomes clear, and an important structure can be visualized satisfactorily while the amount of bleeding can be reduced. Further, in the related art, two surgeons are required because one surgeon incises an organ with a transducer and the other surgeon coagulates a bleeding portion with an electric scalpel to stop bleeding. However, a single surgeon can perform this operation.

REFERENCE SIGNS LIST

1: brush-like structure
2: range that microwave reaches
3: central conductor
4: external conductor
5: insulator
6: water feed tube
7: aspiration tube
8: site with which tissue is brought into contact
9: hollow tube
10: hollow structure
11: vibrating body
12: transducer

The invention claimed is:
1. An organ resection tool, comprising:
a first brush-like structure connected to a central conductor;
a second brush-like structure directly physically connected to an external conductor and not connected to the central conductor;
wherein the first brush-like structure is capable of radiating microwaves generated by a microwave oscillator and the second brush-like structure is capable of receiving the microwaves simultaneously, wherein the microwaves radiate within a microwave irradiation range;

wherein the microwaves generated by the microwave oscillator are transmittable to the first brush-like structure via the central conductor, the first brush-like structure is capable of radiating the microwaves within the microwave irradiation range, the second brush-like structure is capable of receiving the microwaves if the microwaves are within the microwave irradiation range and transferring the microwaves to the external conductor;

wherein the second brush-like structure comprises a plurality of brush units which each radiate outward to a tip portion of the organ resection tool;

wherein at least one from the group consisting of the first brush-like structure and the second brush-like structure has a stiffness and elasticity capable of scraping an organ and applying a pressure to living tissue when brought into contact with the living tissue.

2. The organ resection tool according to claim 1, wherein the central conductor avoids contact with the external conductor through intermediation of an insulator or via an air gap.

3. The organ resection tool according to claim 2, comprising the following configuration:
(1) the central conductor having a cylindrical shape;
(2) the insulator covering a part or all of the central conductor; and
(3) the external conductor covering a part or all of the insulator.

4. The organ resection tool according to claim 2, comprising the following configuration:
(1) the central conductor having a cylindrical shape, wherein the cylindrical shape defines a hollow tube;
(2) the insulator covering a part or all of the central conductor; and
(3) the external conductor covering a part or all of the insulator.

5. The organ resection tool according to claim 4, wherein the hollow tube comprises an aspiration tube and/or a water feed tube.

6. The organ resection tool according to claim 2, comprising the following configuration:
(1) the central conductor having a cylindrical shape, wherein the cylindrical shape defines a hollow structure;
(2) the insulator covering a part or all of the central conductor; and
(3) the external conductor covering a part or all of the insulator.

7. The organ resection tool according to claim 1, wherein the at least one from the group consisting of the first brush-like structure and the second brush-like structure is made of iron, copper, titanium, stainless steel, phosphor bronze, or brass.

8. The organ resection tool according to claim 1, wherein a length of one piece of the at least one from the group consisting of the first brush-like structure and the second brush-like structure falls within a range of from 0.5 mm to 25 mm, a range of from 1.0 mm to 20 mm, or a range of from 5.0 mm to 15 mm.

9. The organ resection tool according to claim 1, wherein a diameter of one piece of the at least one from the group consisting of the first brush-like structure and the second brush-like structure falls within a range of from 0.1 mm to 0.5 mm, a range of from 0.2 mm to 0.5 mm, or a range of from 0.3 mm to 0.5 mm.

10. The organ resection tool according to claim 1, wherein an entire horizontal width of the at least one from the group consisting of the first brush-like structure and the second brush-like structure falls within a range of from 0.2 mm to 3 cm, a range of from 0.5 mm to 2.0 cm, a range of from 0.6 mm to 1.5 cm, or a range of from 0.7 mm to 11 mm.

11. The organ resection tool according to claim 1, wherein the plurality of brush units of the second brush-like structure comprises one or a plurality of rows of a transverse brush, a random arrangement brush, one or a plurality of rows of a circular arrangement brush, or one or a plurality of rows of a semi-circular arrangement brush.

12. The organ resection tool according to claim 1, wherein the second brush-like structure has a loop shape, and is curved in an inward direction at a tip end of the brush-like structure.

13. The organ resection tool according to claim 1, further comprising a vibrator capable of vibrating the at least one from the group consisting of the first brush-like structure and the second brush-like structure.

14. The organ resection tool according to claim 1, wherein both the first brush-like structure and the second brush-like structure each have the stiffness and elasticity capable of scraping the organ and are capable of applying the pressure to the living tissue when being brought into contact with the living tissue.

15. The organ resection tool of claim 1, wherein the second brush-like structure is capable of influencing the microwave irradiation range.

16. The organ resection tool of claim 1, wherein the first brush-like structure is directly physically connected to the central conductor.

17. The organ resection tool of claim 1, wherein the first brush-like structure and the second brush-like structure are arranged coaxially without intersecting one another when projected onto a two-dimensional plane with respect to axes of the organ resection tool.

18. The organ resection tool of claim 1, wherein the plurality of brush units each are straight structures that extend to the tip portion.

* * * * *